US010232318B2

(12) United States Patent
Miyahara et al.

(10) Patent No.: US 10,232,318 B2
(45) Date of Patent: Mar. 19, 2019

(54) DEFECT DETECTION METHOD FOR MONOLITHIC SEPARATION MEMBRANE STRUCTURES, REPAIR METHOD, AND MONOLITHIC SEPARATION MEMBRANE STRUCTURES

(71) Applicant: NGK Insulators, Ltd., Nagoya (JP)

(72) Inventors: Makoto Miyahara, Nagoya (JP); Makiko Ichikawa, Nagoya (JP); Kenji Yajima, Nagoya (JP); Shinji Nakamura, Nagoya (JP); Ryujiro Nagasaka, Nagoya (JP)

(73) Assignee: NGK Insulators, Ltd., Nagoya (JP)

( * ) Notice: Subject to any disclaimer, the term of this patent is extended or adjusted under 35 U.S.C. 154(b) by 300 days.

(21) Appl. No.: 14/661,319

(22) Filed: Mar. 18, 2015

(65) Prior Publication Data

US 2015/0190755 A1 Jul. 9, 2015

Related U.S. Application Data

(63) Continuation of application No. PCT/JP2013/075331, filed on Sep. 19, 2013.

(30) Foreign Application Priority Data

Sep. 28, 2012 (JP) .................................. 2012-218220

(51) Int. Cl.
*B32B 33/00* (2006.01)
*B29C 73/00* (2006.01)
(Continued)

(52) U.S. Cl.
CPC ......... *B01D 65/108* (2013.01); *B01D 63/066* (2013.01); *B01D 65/003* (2013.01);
(Continued)

(58) Field of Classification Search
CPC . B28B 11/006; B28B 11/007; C04B 38/0006; C04B 38/0012; F01N 3/0222;
(Continued)

(56) References Cited

U.S. PATENT DOCUMENTS 3,499,062 A * 3/1970 Geary, Jr. ............ B01D 63/021
264/36.17
4,170,695 A * 10/1979 Brown .............. H01M 10/3918
264/36.16
(Continued)

FOREIGN PATENT DOCUMENTS

EP 0 958 852 A1 11/1999
JP 56-133003 A1 10/1981
(Continued)

OTHER PUBLICATIONS

English translation of Written Opinion (PCT/ISA/237) (Application No. PCT/JP2013/075331) dated Oct. 29, 2013.
(Continued)

*Primary Examiner* — Philip C Tucker
*Assistant Examiner* — Brian R Slawski
(74) *Attorney, Agent, or Firm* — Burr & Brown, PLLC

(57) ABSTRACT

Each cell is pressurized with gas from outside of the cell, the amount of permeation of the gas permeated into each cell is measured, and a cell having the amount of permeation greater than (average value of all cells+A) (wherein A is a predetermined value of σ to 6σ, where σ is the standard deviation) is considered to be defective. Alternatively, pressure is reduced for each cell, the degree of vacuum in each cell is measured, and a cell having the degree of vacuum worse than (average value of all cells+A) is considered to be defective. Then, a polymer compound is poured into the defective cells of the monolithic separation membrane structure and cured so that the defective cells are sealed. Alter-
(Continued)

natively, the polymer compound formed in advance as the sealing member is inserted into the defective cells to seal the defective cells.

12 Claims, 7 Drawing Sheets

(51) Int. Cl.
| | | |
|---|---|---|
| B32B 43/00 | (2006.01) | |
| B29C 65/00 | (2006.01) | |
| B32B 37/00 | (2006.01) | |
| B01D 39/00 | (2006.01) | |
| B01D 41/00 | (2006.01) | |
| B01D 45/00 | (2006.01) | |
| B01D 46/00 | (2006.01) | |
| B01D 49/00 | (2006.01) | |
| B01D 50/00 | (2006.01) | |
| B01D 51/00 | (2006.01) | |
| B01D 59/50 | (2006.01) | |
| F01N 3/00 | (2006.01) | |
| F01N 3/02 | (2006.01) | |
| B01D 65/10 | (2006.01) | |
| B01D 63/06 | (2006.01) | |
| B01D 65/00 | (2006.01) | |
| B01D 69/02 | (2006.01) | |
| B01D 71/02 | (2006.01) | |
| B29C 73/02 | (2006.01) | |
| B29C 73/06 | (2006.01) | |
| G01N 15/08 | (2006.01) | |
| G01M 3/32 | (2006.01) | |
| G01M 3/34 | (2006.01) | |
| B32B 3/12 | (2006.01) | |
| B29C 70/76 | (2006.01) | |
| B29K 79/00 | (2006.01) | |
| B29L 31/14 | (2006.01) | |

(52) U.S. Cl.
CPC ......... *B01D 65/102* (2013.01); *B01D 65/104* (2013.01); *B01D 65/106* (2013.01); *B01D 69/02* (2013.01); *B01D 71/021* (2013.01); *B01D 71/027* (2013.01); *B01D 71/028* (2013.01); *B29C 73/02* (2013.01); *B29C 73/06* (2013.01); *G01M 3/3254* (2013.01); *G01M 3/34* (2013.01); *G01N 15/08* (2013.01); *B01D 2325/24* (2013.01); *B29C 70/766* (2013.01); *B29K 2079/08* (2013.01); *B29K 2995/0068* (2013.01); *B29L 2031/14* (2013.01); *B32B 3/12* (2013.01)

(58) Field of Classification Search
CPC ............... F01N 3/2828; F01N 2330/06; F01N 2330/30; Y02T 10/20; B01D 46/2451; B01D 46/2459; B01D 46/2418; B01D 2279/30; Y10T 428/24149; Y10T 428/24157; B29C 70/766; B32B 3/12

USPC ..... 156/60, 64, 69, 77, 78, 89.11, 89.22, 90, 156/94, 242, 244.11, 244.13, 244.15, 156/244.24, 278, 293, 294, 296, 297, 298, 156/303.1, 329, 330, 333; 428/116, 118; 60/311, 297; 55/523, DIG. 30, 385.3, 55/DIG. 10, 282.3, 524, 282.2, 482, 484
See application file for complete search history.

(56) References Cited

U.S. PATENT DOCUMENTS

| | | | | |
|---|---|---|---|---|
| 4,226,921 | A * | 10/1980 | Tsang | B01D 65/106 264/36.16 |
| 4,248,648 | A * | 2/1981 | Kopp | B01D 65/108 156/285 |
| 5,102,434 | A * | 4/1992 | Hijikata | F01N 3/021 55/523 |
| 5,221,388 | A * | 6/1993 | Haubs | B01D 53/22 156/94 |
| 6,065,329 | A | 5/2000 | Fukada et al. | |
| 6,214,227 | B1 * | 4/2001 | Park | B01D 39/2075 210/433.1 |
| 2006/0090651 | A1 | 5/2006 | Liu et al. | |
| 2006/0151926 | A1 * | 7/2006 | Zoeller, III | F01N 3/0222 264/603 |
| 2007/0277511 | A1 * | 12/2007 | Suwabe | B01D 46/0063 60/297 |
| 2008/0105627 | A1 * | 5/2008 | Isomura | B01D 63/066 210/791 |
| 2009/0072431 | A1 * | 3/2009 | Tokumaru | B01D 46/0001 264/177.12 |
| 2010/0184197 | A1 * | 7/2010 | Dong | C12M 21/02 435/257.1 |
| 2012/0272826 | A1 | 11/2012 | Uchikawa et al. | |

FOREIGN PATENT DOCUMENTS

| | | |
|---|---|---|
| JP | 61-000407 A1 | 1/1986 |
| JP | 61-097006 A1 | 5/1986 |
| JP | 02-014084 B2 | 4/1990 |
| JP | 05-184886 A1 | 7/1993 |
| JP | 07-299341 A1 | 11/1995 |
| JP | 08-131786 A1 | 5/1996 |
| JP | 09-192457 A1 | 7/1997 |
| JP | 2000-109690 A1 | 4/2000 |
| JP | 2007-237073 A1 | 9/2007 |
| WO | 2006/069006 A2 | 6/2006 |
| WO | 2006/069006 A3 | 6/2006 |
| WO | 2011/105511 A1 | 9/2011 |

OTHER PUBLICATIONS

International Search Report and Written Opinion (Application No. PCT/JP2013/075331) dated Oct. 29, 2013 (with English translation).
Extended European Search Report (Application No. 13842337.1) dated Jun. 8, 2016.

* cited by examiner

DEFECT DETECTION METHOD FOR MONOLITHIC SEPARATION MEMBRANE STRUCTURES, REPAIR METHOD, AND MONOLITHIC SEPARATION MEMBRANE STRUCTURES

BACKGROUND OF THE INVENTION

1. Field of the Invention

The present invention relates to a defect detection method for monolithic separation membrane structures in which a separation membrane is formed on the inner wall faces of the cells thereof, a repair method, and monolithic separation membrane structures.

2. Description of Related Art

Recently, ceramic filters have been used in order to selectively collect only a specific component from a multi-component mixture (mixed fluid). Since a ceramic filter is superior to an organic polymer filter in mechanical strength, durability, corrosion resistance, and the like, it is preferably used for removing suspended matter, bacteria, powder dust, etc., in a liquid or gas in wide fields such as water treatment, exhaust gas treatment, medication, and food fields.

In such a ceramic filter, it is necessary to increase the membrane area (area of the separation membrane) in order to improve water permeability while securing separation performance, and, to do so, it is desirable that the filter has a honeycomb shape (monolithic shape). In many cases, the monolithic separation membrane structure means a structure having a round pillar external shape and being provided with a porous substrate having a large number of parallel passages (cells) formed in the axial direction thereof wherein separation membrane having a hole diameter smaller than that of the porous substrate is formed on the inner wall faces forming the cell.

In the case of forming a separation membrane on the monolithic substrate (honeycomb structure), part of the cells having a defect influences the quality of products even if a good membrane is formed on many cells. The Patent Document 1 discloses a defect inspection method and a defect repair method for a ceramic membrane.

CITATION LIST

Patent Documents

[Patent Document 1] JP-A-H8-131786

SUMMARY OF THE INVENTION

Problem to be Solved by the Invention

However, the defect inspection method and the defect repair method of the Patent Document 1 is a method of inspecting defects on the outer face of the tube and repairing them.

The detection of defects caused inside a cell of a monolithic substrate is not possible by visual inspection. In addition, there has been no simple repair method for defects occurred inside the cells of the monolithic substrate.

An objective of the present invention is to provide a simple defect detection method for detecting a defect of a monolithic separation membrane structure in which a separation membrane is formed on the cells. In addition, there is provided a monolithic separation membrane structure repair method for repairing a monolithic separation membrane structure having a defective cell. Furthermore, there is provided a monolithic separation membrane structure where the defect is repaired.

Means for Solving the Problem

In order to solve the aforementioned problems, according to the present invention, there are provided the following defect detection method for monolithic separation membrane structures, repair method, and monolithic separation membrane structures.

According to a first aspect of the present invention, a monolithic separation membrane structure comprising: a monolithic substrate having a plurality of cells defined and formed by porous partition walls from one end face to the other end face in the longitudinal direction, and a separation membrane formed on inner wall faces of the cells, wherein at least both end portions of part of the cells are sealed with sealing members through which fluid does not pass is provided.

According to a second aspect of the present invention, the monolithic separation membrane structure according to the first aspect is provided, wherein the sealing members are of polymer compound.

According to a third aspect of the present invention, the monolithic separation membrane structure according to the second aspect is provided, wherein the polymer compound is a synthetic resin.

According to a fourth aspect of the present invention, the monolithic separation membrane structure according to the third aspect is provided, wherein the synthetic resin is one of epoxy, silicon-based, and fluorine-based resins.

According to a fifth aspect of the present invention, the monolithic separation membrane structure according to any one of the first to fourth aspects is provided, wherein the separation membrane is formed of an inorganic material.

According to a sixth aspect of the present invention, the monolithic separation membrane structure according to the fifth aspect is provided, wherein the inorganic material is one of zeolite, carbon, and silica.

According to a seventh aspect of the present invention, the monolithic separation membrane structure according to any one of the first to sixth aspects is provided, wherein the monolithic substrate is of a porous ceramic.

According to an eighth aspect of the present invention, the monolithic separation membrane structure according to any one of the first to seventh aspects is provided, wherein the withstand pressure for use is 1 MPa or more.

According to a ninth aspect of the present invention, a repair method for a monolithic separation membrane structure, wherein at least both end portions of at least part of cells among defective cells of the monolithic separation membrane structure in which a separation membrane is formed on inner wall faces of cells of a monolithic substrate having a plurality of cells defined and formed by porous partition walls from one end face to the other end face in the longitudinal direction are sealed with sealing members through which fluid does not pass is provided.

According to a tenth aspect of the present invention, the repair method for a monolithic separation membrane structure according to the ninth aspect is provided, wherein a polymer compound as the sealing member is poured into the defective cells of the monolithic separation membrane structure and cured to seal the defective cells.

According to an eleventh aspect of the present invention, the repair method for a monolithic separation membrane structure according to the ninth aspect is provided, wherein a polymer compound formed in advance as the sealing member is inserted into the defective cells of the monolithic separation membrane structure to seal the defective cells.

According to a twelfth aspect of the present invention, a defect detection method for a monolithic separation membrane structure in which a separation membrane is formed on inner wall faces of cells of a monolithic substrate having a plurality of cells defined and formed by porous partition walls from one end face to the other end face in the longitudinal direction, wherein each cell is pressurized with gas from outside of the cell, an amount of permeation of the gas permeated into each cell is measured, and a cell having the amount of permeation greater than "average value of all cells+A" (wherein A is a predetermined value of $\sigma$ to $6\sigma$, where $\sigma$ is the standard deviation) is considered to be defective is provided.

According to a thirteenth aspect of the present invention, a defect detection method for a monolithic separation membrane structure in which a separation membrane is formed on inner wall faces of cells of a monolithic substrate having a plurality of cells defined and formed by porous partition walls from one end face to the other end face in the longitudinal direction, wherein pressure is reduced for each cell, a degree of vacuum in each cell is measured, and a cell having the degree of vacuum worse than "average value of all cells+A" (wherein A is a predetermined value of $\sigma$ to $6\sigma$, where $\sigma$ is the standard deviation) is considered to be defective is provided.

Effect of the Invention

The defect detection method for monolithic separation membrane structure of the present invention has no oversight because the defects are detected as a numerical value. Since the repair method for monolithic separation membrane structure of the present invention is not a method where the defects are directly repaired, but a method where a cell itself is filled, it enables to repair easily in a short period of time. In particular, the separation coefficient of the entire monolithic separation membrane structure can be enhanced by detecting the cells having a larger amount of defects in comparison with the other cells and repairing the cells. Repairing only the cell(s) having defects improves the product yield.

DETAILED DESCRIPTION OF THE INVENTION

Figure 1:
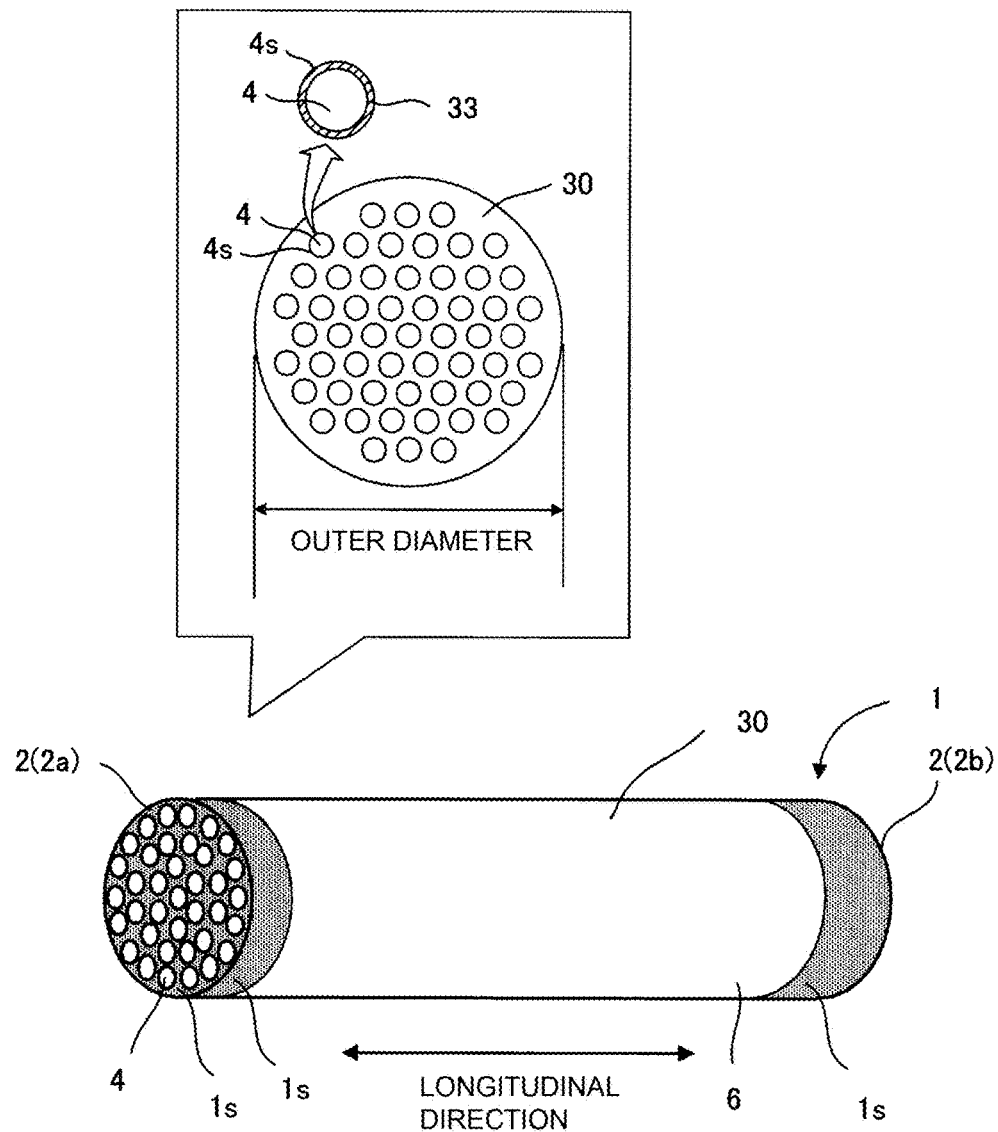
FIG. 1 is a view showing an embodiment of a monolithic separation membrane structure of the present invention.

Hereinbelow, embodiments of the present invention will be described with referring to drawings. The present invention is not limited to the following embodiments, and changes, modifications, and improvements may be added as long as they do not deviate from the scope of the invention.

A defect detection method for monolithic separation membrane structures of the present invention is a defect detection method for a monolithic separation membrane structure in which a separation membrane is formed on the inner wall faces of the cells of the monolithic substrate having a plurality of cells defined and formed by porous partition walls from one end face to the other end face in the longitudinal direction. Each cell is pressurized with gas from outside of the cell, the amount of permeation of the gas permeated into each cell is measured, and a cell having a permeation amount greater than "average value of all cells+A" (wherein A is a predetermined value of $\sigma$ to $6\sigma$, where $\sigma$ is the standard deviation) is considered to be defective. That is, such a cell is considered as a cell having more defects than the other cells (defective cell) and an objective to be repaired.

Alternatively, pressure is reduced for each cell, the degree of vacuum in the cell is measured, and a cell with a degree of vacuum value worse than "average value of all cells+A" (wherein A is a predetermined value of $\sigma$ to $6\sigma$, where $\sigma$ is the standard deviation) is considered to be defective. That is, such a cell is considered as a cell (defective cell) having more defects than the other cells and an object of repair.

Though the value of A may be determined within the range of $\sigma$ to $6\sigma$, $\sigma$ to $5\sigma$ is preferable, and $\sigma$ to $3\sigma$ is preferable when separation accuracy is required. The preferable values are $2\sigma$ in a field where a relatively high separation performance is required, such as gas separation or anhydration in a product-manufacturing step, and $5\sigma$ in a field where the costs of the separation membrane structures are given more weight to than separation accuracy, such as effluent treatment or exhaust gas collection.

The defect detection of cells may be performed in either of permeation amount measurement and degree of vacuum measurement. It is to be noted that the standard deviation $\sigma$ is obtained by the following formula, where x is a gas permeation amount (or degree of vacuum) of each cell, and n is the number of cells where the gas permeation amount (or degree of vacuum) is measured.

$$\sigma = \sqrt{\frac{n\sum_{i=1}^{n} x_i^2 - \left(\sum_{i=1}^{n} x_i\right)^2}{n(n-1)}}$$ [Formula 1]

The repair method for monolithic separation membrane structures of the present invention is a repair method of a monolithic substrate having a plurality of cells defined and formed by porous partition walls from one end face to the other end face in the longitudinal direction. The monolithic separation membrane structure having defects is repaired by sealing at least the both end portions of at least part of the cells having defects of the monolithic separation membrane structure with sealing members through which fluid does not pass. Specifically, a polymer compound as the sealing member is poured into the defective cells of the monolithic separation membrane structure having a separation membrane formed on the inner wall faces of the cells and cured to seal the defective cell. Alternatively, a polymer compound formed in advance as the sealing member is inserted into the defective cell to seal the defective cell. It is to be noted that it is preferable to seal all the defective cells in the case where a high separation performance of the product is required.

A monolithic separation membrane structure repaired by a repair method for monolithic separation membrane structures of the present invention includes a monolithic substrate having a plurality of cells defined and formed by porous partition walls from one end face to the other end face in the longitudinal direction and a separation membrane formed on the inner wall faces of the cells, where at least the both end portions of part of the cells are sealed with sealing members through which fluid does not passes.

Hereinbelow, more specific descriptions will be given. A monolithic separation membrane structure will firstly be described, and then a defect detection method and a repair method for the monolithic separation membrane structure will be described.

1. Monolithic Separation Membrane Structure

FIG. 1 shows an embodiment of a monolithic separation membrane structure 1 of the present invention. The monolithic separation membrane structure 1 (hereinbelow also referred to simply as a separation membrane structure) has a monolith-shaped substrate 30 (monolithic substrate) and a separation membrane 33 (in the present specification, the substrate 30 is also referred to as a monolithic porous body 9 (or simply as a porous body 9)). The "monolithic substrate" in the present invention means a substrate having a shape where a plurality of cells are formed from one end face to the other end face in the longitudinal direction or a honeycomb shape.

The separation membrane structure 1 has porous partition walls 3 having a large number of pores formed therein, and cells 4 functioning as fluid passages are formed by the partition walls 3. Hereinbelow, the substrate 30, the separation membrane 33, and the like will be described in detail.

(Substrate)

There is no limitation on the material for the substrate 30 as long as it is porous, such as ceramics, metals, and resins. Of these, porous ceramics are preferable. It is more preferable that the aggregate particles are of alumina ($Al_2O_3$), titania ($TiO_2$), mullite ($Al_2O_3$—$SiO_2$), Scherben, cordierite ($Mg_2Al_4Si_5O_{18}$), or the like. Of these, alumina is furthermore preferable because a raw material (aggregate particles) having a controlled particle size can easily be obtained, a stable kneaded material can be formed, and it has high corrosion resistance.

The substrate 30 has a round pillar external shape and an outer peripheral face 6, however the entire shape and size of the substrate 30 are not particularly limited as long as they do not inhibit the separation function. As examples of the entire shape, there can be mentioned a round pillar (cylindrical) shape, a square pillar shape (a tubular shape having a square cross section perpendicular to the central axis), a triangular pillar shape (a tubular shape having a triangular cross section perpendicular to the central axis), and the like. Of these, a round pillar shape is preferable because of easy extrusion, little firing deformation, and easy sealing with the housing. In the case of being used for microfiltration or ultrafiltration, preferred is a round pillar shape where the diameter in a cross section perpendicular to the central axis is 30 to 220 mm and the length in the central axial direction is 150 to 2000 mm.

The substrate 30 has a plurality of cells 4 functioning as fluid passages defined and formed by porous partition walls 3 from one end face 2a to the other end face 2b in the longitudinal direction. The substrate 30 has 30 to 2500 cells 4 extending through to both end sides in the longitudinal direction and parallel to the longitudinal direction.

As the cross-sectional shape of the cell 4 of the substrate 30 (shape in a cross section perpendicular to the extension direction of the cells 4), there can be mentioned, for example, a circle, an ellipse, and a polygon. As the polygon, there can be mentioned a quadrangle, a pentagon, a hexagon, a triangle, and the like. It is to be noted that the extension direction of the cells 4 is the same as the central axial direction in the case where the substrate 30 has a round pillar (cylindrical) shape.

In the case where the cross-sectional shape of the cell 4 of the substrate 30 is circular, the diameter of the cell 4 is preferably 1 to 5 mm. The diameter of 1 mm or more enables to secure the membrane area sufficiently. The diameter of 5 mm or less enables the strength to be sufficient.

It is also possible to provide a plurality of layer where the average particle size is changed on the substrate 30. Specifically, an intermediate layer and a surface layer having a small average particle size and a surface layer can be laminated on the substrate 30. In the case of providing the intermediate layer and the surface layer, these layers are included in the porous body 9.

It is preferable that sealing portions 1s are disposed on both the end faces 2, 2 of the substrate 30. Such disposition of sealing portions is enables to inhibit part of mixture from directly flowing into the inside of the substrate 30 from the end face 2 of the substrate 30 without passing through the separation membrane 33, thereby inhibiting the mixture from being mixed with gas or the like which has passed through the separation membrane 33 and being discharged from the outer peripheral face 6. Examples of the sealing portion 1s include a glass seal and a metal seal.

(Separation Membrane)

The separation membrane 33 has a plurality of pores formed therein and an average pore size smaller than that of the porous body 9 (substrate 30 or including the intermediate layer and the surface layer if provided) and is disposed on the wall faces (inner wall faces 4s) inside the cells 4.

The average pore size of the separation membrane 33 can appropriately be determined depending on the required filtration performance or separation performance (particle size of the substance to be removed). For example, in the case of a ceramic filter used for microfiltration or ultrafiltration, it is preferably 0.01 to 1.0 μm. In this case, the average pore size of the separation membrane 33 is a value measured by the air flow method described in ASTM F316.

As the separation membrane 33, there may be employed a gas separation membrane or a reverse osmosis membrane. Though the separation membrane 33 is not particularly limited, it is preferably formed of an inorganic material. More specifically, as the inorganic material, there can be mentioned zeolite, carbon, silica, and the like.

In the case where the separation membrane 33 is a zeolite membrane, as the zeolite, there may be used such a zeolite having a crystal structure including LTA, MFI, MOR, FER, FAU, DDR, CHA, and BEA. In the case where the separation membrane 33 is of a DDR type zeolite, it can be used particularly as a gas separation membrane used for selectively separating carbon dioxide.

2. Separation Method

Figure 2A:
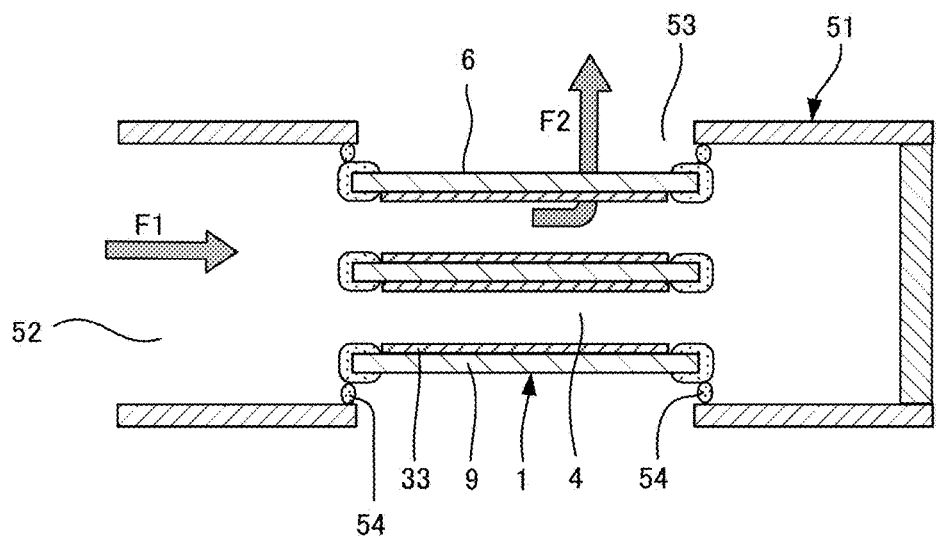
FIG. 2A is a schematic view showing an embodiment where a monolithic separation membrane structure is mounted in the housing and showing a cross section parallel to the direction which the cells of the ceramic separation membrane structure extend.

Next, a method for separating part of components out of a fluid where plural kinds are mixed by use of a separation membrane structure 1 of the present embodiment will be described. As shown in FIG. 2A, upon separation of a fluid using a separation membrane structure 1 of the present embodiment, it is preferable that the separation membrane structure 1 is housed in a tubular housing 51 having a fluid inlet port 52 and a fluid outlet port 53, so that the fluid to be treated F1 allowed to flow in from the fluid inlet port 52 of the housing 51 is separated by the separation membrane structure 1, and the separated fluid to be treated (treated fluid F2) is discharged from the fluid outlet port 53.

When the separation membrane structure 1 is housed in the housing 51, as shown in FIG. 2A, it is preferable to seal a gap between the separation membrane structure 1 and the housing 51 with the sealing members 54, 54 at both the end portions of the separation membrane structure 1. Though there is no particular limitation on the sealing member 54, for example, an O-ring can be mentioned.

All the fluid to be treated F1 which flows into the housing 51 from the fluid inlet port 52 enters the cells 4 of the separation membrane structure 1, and the fluid to be treated F1 which have flown into the cells 4 passes through the separation membrane 33 and penetrates into the substrate 30 as the treated fluid F2. Then, it flows out from the outer peripheral face 6 of the substrate 30 to the outside of the substrate 30 and is discharged to the outside (external space) from the fluid outlet port 53. The fluid to be treated F1 and the treated fluid F2 can be inhibited from being mixed together by the sealing members 54, 54.

Figure 2B:
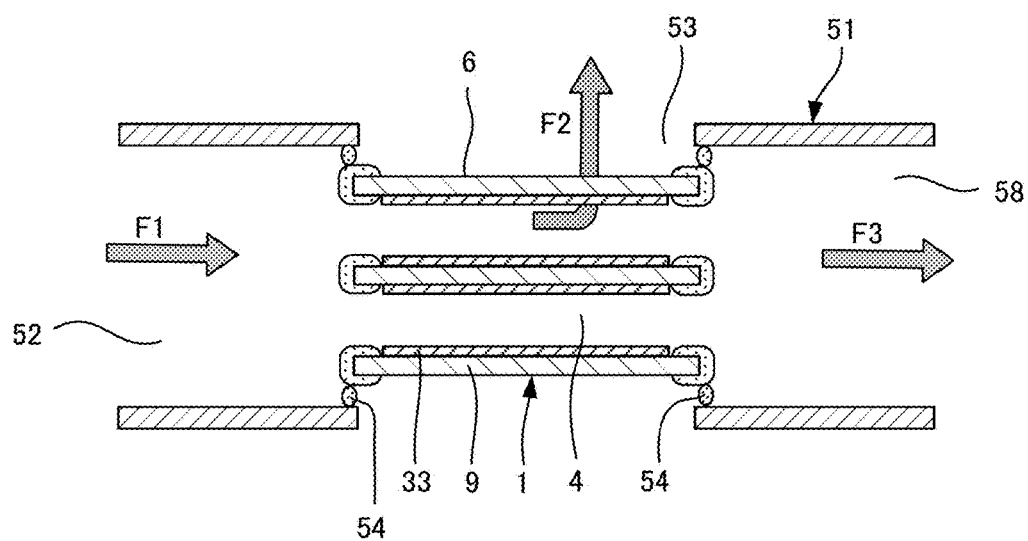
FIG. 2B is a schematic view showing another embodiment where a monolithic separation membrane structure is mounted in the housing and showing a cross section parallel to the direction which the cells of the ceramic separation membrane structure extend.

FIG. 2B shows another embodiment where a separation membrane structure 1 is mounted in the housing 51. As shown in FIG. 2B, the separation membrane structure 1 is housed in the tubular housing 51 having a fluid inlet port 52 and fluid outlet ports 53, 58. In this embodiment, the fluid to be treated F1 allowed to flow in from the fluid inlet port 52 of the housing 51 can be separated by the separation membrane structure 1, the separated fluid to be treated (treated fluid F2) can be discharged from the fluid outlet port 53, and the rest (fluid F3) can be discharged from the fluid outlet port 58. Since the fluid F3 can be discharged from the fluid outlet port 58, the flow rate of the fluid to be treated F1 can be increased in operation, and the permeation flow rate of the treated fluid F2 can be increased.

3. Manufacturing Method (Substrate)

Next, a method for manufacturing a separation membrane structure 1 of the present invention will be described. First, a raw material for a porous body is formed. It is extruded by the use of a vacuum extruder, for example. Thus an unfired monolithic substrate 30 having cells 4 is obtained. Alternatively, there are press forming, cast forming, and the like, which may appropriately be selected. Next, the unfired substrate 30 is fired at 900 to 1450° C., for example. It is to be noted that an intermediate layer and a surface layer may be formed in the cells 4.

(Separation Membrane)

Next, the separation membrane 33 is formed on the inner wall faces 4s of the cells 4. Descriptions will be given with the cases of forming a zeolite membrane, a silica membrane, and a carbon membrane as the separation membrane 33 as examples.

(Zeolite Membrane)

Figure 4:
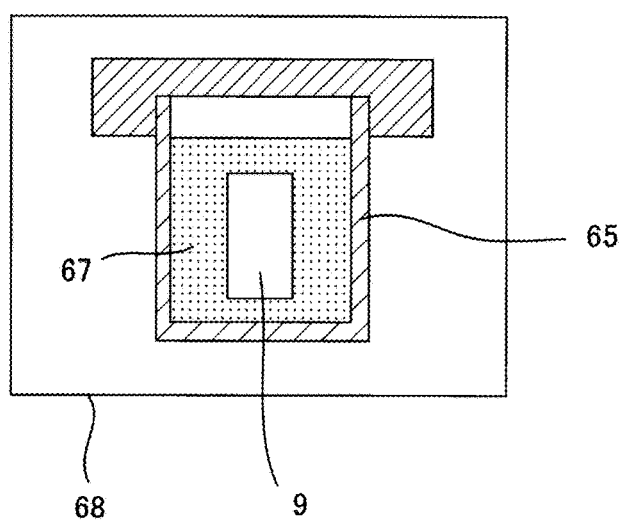
FIG. 4 is a schematic view showing an embodiment of a membrane formation step, where a zeolite membrane is formed on a porous body by hydrothermal synthesis.

Descriptions will be given on the case where a zeolite membrane is disposed as the separation membrane 33. A zeolite membrane used in the present invention can be synthesized by a conventionally known method. For example, as shown in FIG. 4, a raw material solution (sol 67) of a silica source, an alumina source, an organic template, an alkali source, water, and the like is prepared, and, after a porous body 9 (substrate 30) and the raw material solution (sol 67) prepared are put in a pressure resistant vessel 65, these are put in a dryer 68 and heated at 100 to 200° C. for 1 to 240 hours to perform a heating treatment (hydrothermal synthesis), thereby forming a zeolite membrane.

At this time, it is preferable to apply zeolite as seed crystals onto the porous body 9 (substrate 30) in advance. Next, the porous body 9 having a zeolite membrane formed thereon is washed with water or warm water of 80 to 100° C. and then taken out to be dried at 80 to 100° C. Then, the porous body 9 is put in an electric furnace and heated at 400 to 800° C. for 1 to 200 hours in an air atmosphere to burn away the organic template in the pores of the zeolite membrane. Thus, the zeolite membrane can be formed.

As the silica source, there can be mentioned colloidal silica, tetraethoxysilane, liquid glass, silicon alkoxide, fumed silica, precipitated silica, and the like.

The organic template is used for forming the pore structure of zeolite. Though it is not particularly limited, there can be mentioned organic compounds such as tetraethylammonium hydroxide, tetraethylammonium bromide, 1-adamantanamine, tetrapropylammonium hydroxide, tetrapropylammonium bromide, and tetramethylammonium hydroxide.

As the alkali source, there can be mentioned alkali metals such as sodium hydroxide, lithium hydroxide, potassium hydroxide; alkali earth metals such as magnesium hydroxide and calcium hydroxide; quaternary ammonium hydroxide: and the like.

The method for forming the zeolite membrane can appropriately be applied to the zeolite having a crystal structure of LTA, MFI, MOR, FER, FAU, DDR, CHA, BEA, or the like.

(Silica Membrane)

Descriptions will be given on the case where a silica membrane is disposed as a sealing member 33 on the inner wall faces 4s of the cells 4. A precursor solution (silica sol solution) for forming a silica membrane can be prepared by subjecting tetraethoxysilane to hydrolysis in the presence of nitric acid to obtain a sol solution, which is then diluted with ethanol. Instead of diluting with ethanol, dilution with water is also possible. Then, the precursor solution (silica sol solution) to form the silica membrane is poured from above the porous body 9 and allowed to pass through the cells 4 or subjected to general dipping to allow the precursor solution to adhere to the inner wall faces of the cells 4. Then, the temperature is raised at a rate of 10 to 100° C./hour, and, after it was maintained at 350 to 600° C. for 1 to 100 hours, it was lowered at a rate of 10 to 100° C./hour. Such operations of pouring, drying, raising temperature, and lowering temperature are repeated 3 to 10 times to form the silica membrane. Thus, a separation membrane structure 1 having a silica membrane as the separation membrane 33 can be obtained.

(Carbon Membrane)

Descriptions will be given on the case of disposing a carbon membrane as a separation membrane 33 on the inner wall faces 4s of the cells 4. In this case, a membrane may be formed by bringing the precursor solution for forming a carbon membrane into contact with the surface of the porous body 9 by means of dip coating, immersion, spin coating, spray coating, or the like. The precursor solution can be obtained by mixing and dissolving a thermosetting resin such as phenol resin, melamine resin, urea resin, furan resin, polyimide resin, and epoxy resin; a thermoplastic resin such as polyethylene; a cellulose-based resin; or a precursor substance of such a resin into an organic solvent such as methanol, acetone, tetrahydrofuran, NMP, or toluene; water; or the like. Upon forming the precursor solution into a membrane, an appropriate heating treatment may be performed according to the kind of the resin contained in the solution. Thus obtained precursor membrane is carbonated to obtain a carbon membrane.

Figure 5:
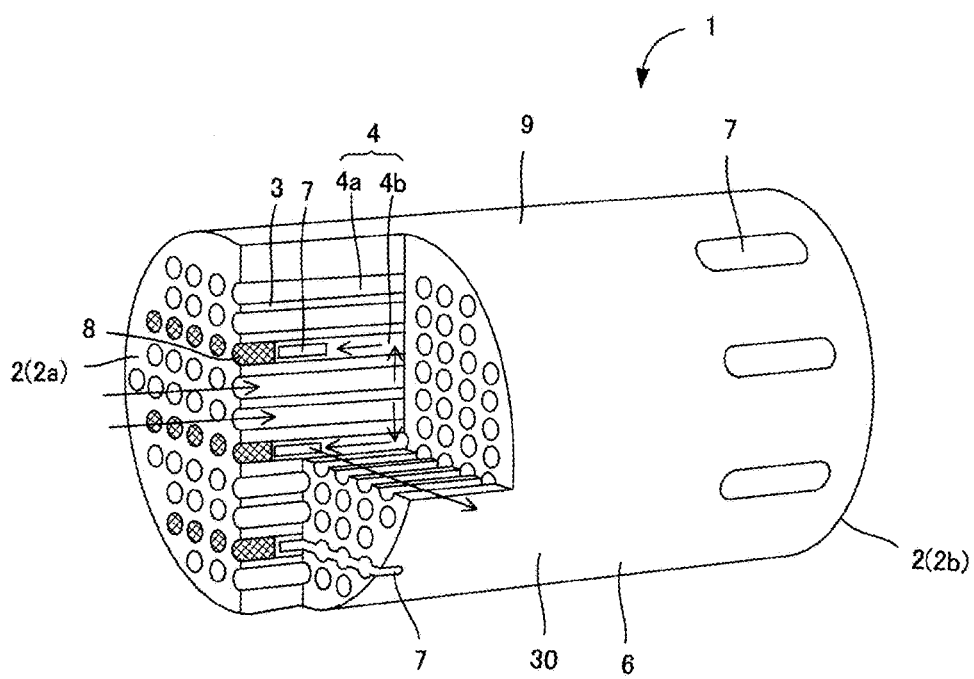
FIG. 5 is a perspective view showing another embodiment of a monolithic separation membrane structure of the present invention.

FIG. 5 shows another embodiment of a monolithic separation membrane structure 1 of the present invention. The present embodiment has a plurality of separation cells 4a extending through from one end face 2a to the other end face 2b formed in rows and a plurality of water collection cells 4b formed from the one end face 2a to the other end face 2b in rows. The separation cells 4a and the water collection cells 4b of the separation membrane structure 1 have a circular cross-sectional shape. Both the end faces 2a, 2b of the separation cells 4a are open (left open). In the water collection cells 4b, the openings of both the end faces 2a, 2b are plugged with plugging members to form plugging portions 8, and discharge passages 7 are provided so that the water collection cells 4b communicate with the external space. In addition, the separation membrane 33 is disposed on the surfaces of the inner wall faces 4s of the separation cells 4a.

4. Defect Detection Method

The separation membrane structure 1 manufactured as described above may have defects in the separation membrane 33. When the separation membrane 33 has a defect, it cannot be used as a product. Therefore, it is necessary to detect presence/absence of a defect. First, a defect detection method will be described using FIG. 6. The first defect detection method is a method where each cell 4 is pressurized with gas from outside of the cell 4, an amount of permeation of the gas permeated into each cell 4 is measured, and a cell 4 having the amount of permeation greater than "average value of all cells+A" (wherein A is a predetermined value of $\sigma$ to $6\sigma$, where $\sigma$ is the standard deviation) is considered to be defective.

Figure 6:
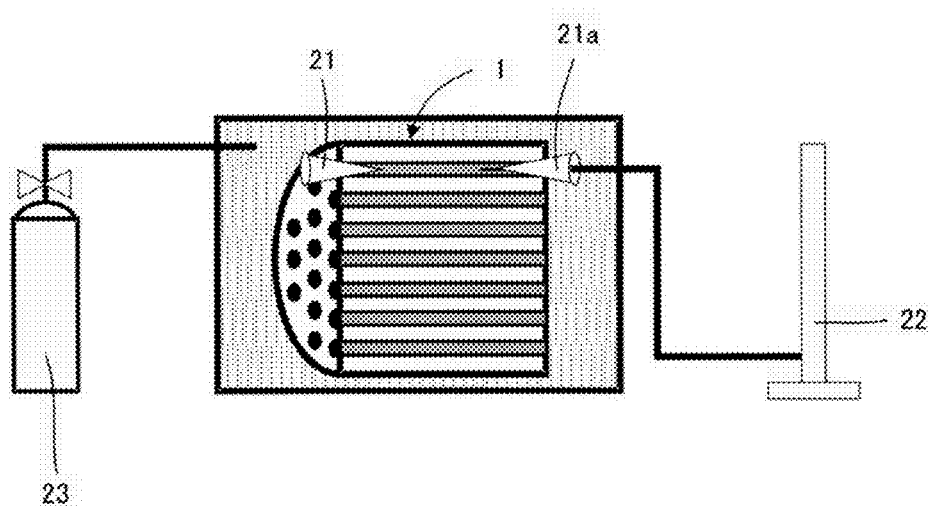
FIG. 6 is a view for illustrating measurement of gas permeation amount.

As shown in FIG. 6, one end of a cell 4 to be measured is plugged with a plug 21 such as a silicon plug, and the other end of the cell 4 is connected to a flowmeter 22 such as a soap-film flowmeter 22 (the plug 21a on the other side has a hole formed therein, and a tube is connected to the flowmeter 22). It is preferable that the plug 21 is made of resin having a conical or cone-frustum shape. The use of such a plug 21 enables to enhance airtightness. Then, a gas (evaluation gas) having a larger molecular size than the pore size of the zeolite, such as $CF_4$, is supplied (e.g., 0.2 MPa) from the gas cylinder 23 from the outer surface of the separation membrane structure 1, and the time for a certain amount (e.g., 0.5 cc) of the evaluation gas leaked from the cell 4 is measured to calculate the permeation amount of the evaluation gas. The measurement is performed for all the cells 4, and the standard deviation $\sigma$ of the gas permeation amount of the evaluation gas is calculated from the permeation amount data of the evaluation gas for each cell 4.

The cells 4 where the permeation amount is larger than "average value of all cells+A" are cells 4 having a large influence on the decrease of the separation coefficient. Therefore, detection of low separation coefficient cells having more defects and lower separation coefficient than the other cells 4 by the use of $\sigma$ to $6\sigma$ enables to selectively detect the cells 4 having a large influence on the decrease of separation coefficient. Detection and repair of the low separation coefficient cells (defective cells) in one monolithic separation membrane structure 1 enable to raise the separation coefficient of the entire monolithic separation membrane structure.

Next, the second defect detection method will be described. The second defect detection method is a method where pressure is reduced for each cell 4, the degree of vacuum in each cell 4 is measured, and a cell 4 having the degree of vacuum worse than "average value of all cells+A" (wherein A is a predetermined value of $\sigma$ to $6\sigma$, where $\sigma$ is the standard deviation) is considered to be defective.

Figure 7:
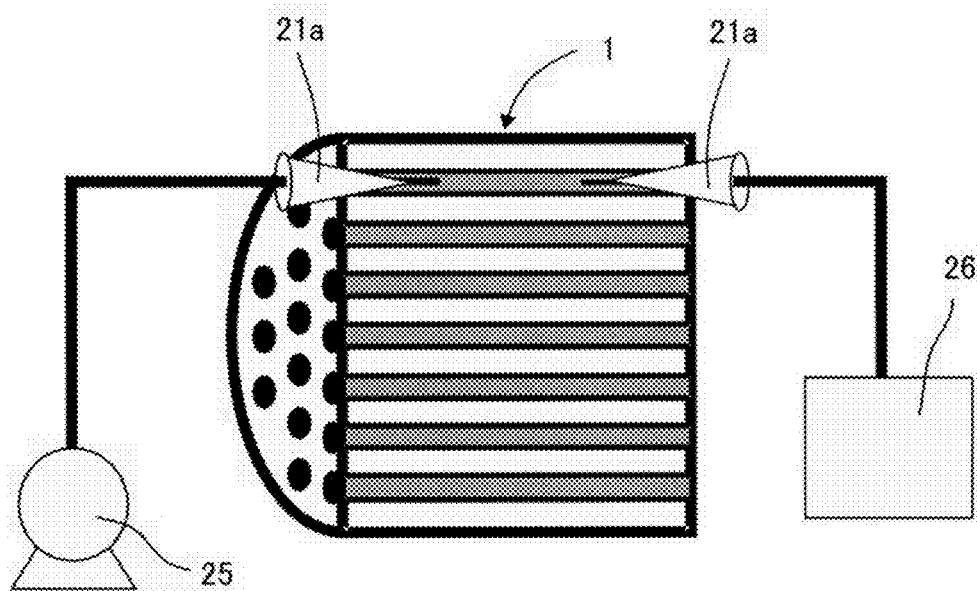
FIG. 7 is a view for illustrating measurement of degree of vacuum.

As shown in FIG. 7, both the ends of a cell 4 to be measured are plugged with plugs 21a such as silicon plugs having a hole formed therein. It is preferable that the plug 21a is made of resin having a conical or cone-frustum shape. The use of such a plug 21a enables to enhance airtightness. A vacuum pump 25 is connected to the plug 21a on one side, and a vacuum gauge 26 is connected to the plug 21a on the other side. The inside of the cell 4 is subjected to vacuum drawing by a vacuum pump 25 and the achieved degree of vacuum inside the cell 4 is measured. The measurement is performed for all the cells 4, and the standard deviation $\sigma$ of the degree of vacuum is calculated from the data of the achieved degree of vacuum for each cell 4.

The cells 4 with a degree of vacuum worse than "average value of all cells+A" are cells 4 having a large influence on the decrease of the separation coefficient. Therefore, detection of low separation coefficient cells having more defects and lower separation coefficient than the other cells 4 by the use of $\sigma$ to $6\sigma$ enables to selectively detect the cells 4 having a large influence on the decrease of separation coefficient. That is, detection and repair of the low separation coefficient cells (defective cells) in one monolithic separation membrane structure 1 enable to raise the separation coefficient of the entire monolithic separation membrane structure.

It is to be noted that the defect detection method of the present invention can detect low separation coefficient cells (defective cells) having particularly low separation coefficient in comparison with the other cells 4 in one monolithic separation membrane structure.

5. Defect Repair Method

A separation membrane structure which is considered to be defective as described above cannot be used as a product as it is. Therefore, a method for repairing defects will be described.

Figure 8:
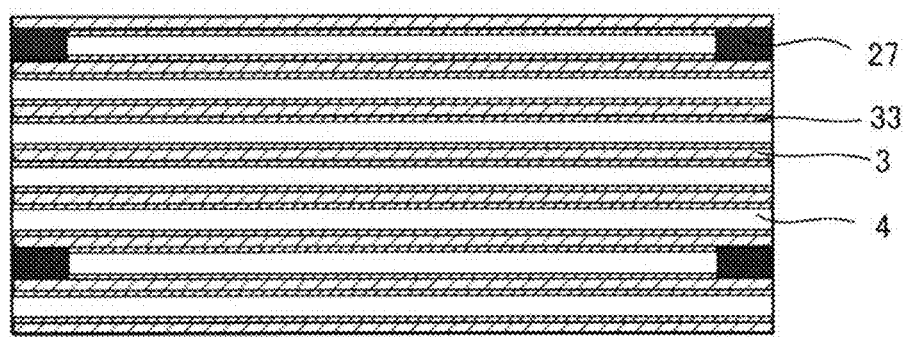
FIG. 8 is a cross-sectional view of a separation membrane structure repaired by pouring a polymer compound into defective cells.

The first repair method for a monolithic separation membrane structure of the present invention is a method where a polymer compound 27 having plasticity and fluidity is poured into the defective cells 4 of the monolithic separation membrane structure 1 having a separation membrane 33 formed on the inner wall faces of the cells 4 and cured to seal the defective cells. FIG. 8 shows a cross-sectional view of a separation membrane structure 1 repaired by pouring a polymer compound 27 as a sealing member through which a fluid does not pass into the defective cells and curing it. It is preferable that at least the both end portions of part of the cells 4 are sealed with the polymer compound 27. Furthermore, it is preferable that the polymer compound 27 is poured into each of the end portions of the cells 4 up to 1 mm or more and cured. All the inside of defective cells 4 may be filled with the polymer compound 27. Since this inhibits the mixture (mixed gas, mixed liquid, etc.) from entering the defective cells 4, degradation in separation performance can be inhibited. It is to be noted that the sealing with the polymer compound 27 in FIG. 8 is performed for separation cells 4a in FIG. 5, and it is different from the plugging portions 8 in the water collection cells 4b of FIG. 5.

Figure 9:
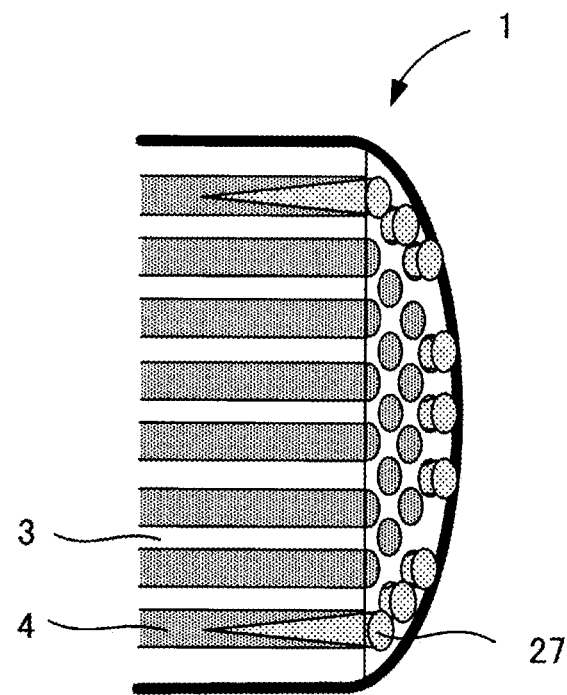
FIG. 9 is a view showing a separation membrane structure where defective cells are sealed by inserting polymer compounds formed in advance into defective cells.

The second repair method for a monolithic separation membrane structure of the present invention is a method where the defective cells 4 are sealed by inserting a polymer compound 27 formed in advance into the defective cells 4. At that time, an adhesive may be used together. FIG. 9 shows a separation membrane structure where a polymer compound formed in advance is inserted in the defective cells. Also in the second method, at least the both end portions of part of cells 4 are sealed with a polymer compound 27.

Since a polymer compound has pressure resistance and chemical resistance, the separation membrane structure 1 where the defective cells 4 are sealed with polymer compound has no problem in use. As the polymer compound, synthetic resin can be mentioned. More specifically, as the synthetic resin, there can be mentioned epoxy, silicone-based, and fluorine-based synthetic resins.

In the separation membrane structure 1 manufactured and repaired in the aforementioned method, the withstand pressure for use, which is the maximum pressure where no defect is caused in the repaired portion (portion sealed with a polymer compound) and the separation membrane 33 even by pressurization, and no degradation in separation performance is caused, is 1 MPa or more. The withstand pressure for use (separation performance retention strength) means the maximum pressure where no degradation in separation performance has occurred after pressurizing the cells of the separation membrane structure 1. That is, when (separation coefficient after pressurization/separation coefficient before pressurization)<1, the separation performance is considered to be degraded, and the maximum pressure where separation performance has not occurred is the withstand pressure for use (separation performance retention strength).

The method for repairing the cell 4 where a permeation amount or a degree of vacuum is deviated from each average value of the present invention can repair the cells 4 having more defects than the other cells 4. Targeting such cells 4 for repair enables to efficiently raise the separation coefficient of the entire monolithic separation membrane structure.

EXAMPLES

Hereinbelow, the present invention will be described in more detail based on Examples. However, the present invention is by no means limited to these Examples.

1. Method for Manufacturing Monolithic Separation Membrane Structure

A monolithic substrate 30 was manufactured, and a separation membrane 33 was formed inside the cells 4. First, manufacturing of the substrate 30 will be described.

(Substrate)

To 100 parts by mass of alumina particles (aggregate particles) having an average particle size of 50 μm were added 20 parts by mass of an inorganic binder (sintering auxiliary agent), water, a dispersant, and a thickener were further added, and mixed and kneaded to prepare a kneaded material. The kneaded material was extruded to produce an unfired monolithic substrate 30.

In the unfired substrate 30, discharge passages 7 passing through the water collection cells 4b from one portion to the other portion of the outer peripheral face 6 were formed (Example 3 only. See FIG. 5).

Then, the substrate 30 was fired. The firing conditions were 1250° C. and 1 hour, and both the temperature rising rate and the temperature falling rate were 100° C./hour.

Each of the porous bodies 9 (substrates 30) of Examples 1 to 3 and 5 to 6 had a round pillar external shape, an outer diameter of 30 mm and a full length of 160 mm and 55 cells having a cell diameter of 2.5 mm (Example 3 had 30 water collection cells 4b).

The porous body 9 (substrate 30) of Example 4 had an outer diameter of 180 mm and a full length of 1000 mm, and 2050 cells with a cell diameter of 2.5 mm.

Next, there were produced samples where one of a DDR membrane, a silica membrane, and a carbon membrane was formed as the separation membrane 33 on the wall faces inside the cells 4 of the porous body 9. Each production method will be described.

Examples 1 to 4

(Formation of DDR Membrane)

As the separation membrane 33, a DDR membrane was formed on the inner wall faces 4s of the cells 4.

(1) Production of Seed Crystal

A DDR type zeolite crystal powder was prepared based on the method for producing DDR type zeolite described in M. J. den Exter, J. C. Jansen, H. van Bekkum, *Studies in Surface Science and Catalysis* vol. 84, Ed. by J. Weitkamp et al., Elsevier (1994) 1159-1166, or JP-A-2004-083375, and the powder was used as it was or by pulverizing it if necessary as seed crystals. After the seed crystals subjected to synthesis or pulverization were dispersed in water, coarse particles were removed to prepare a seed crystal dispersion liquid.

(2) Seeding (Particle Adhesion Step)

Figure 3:
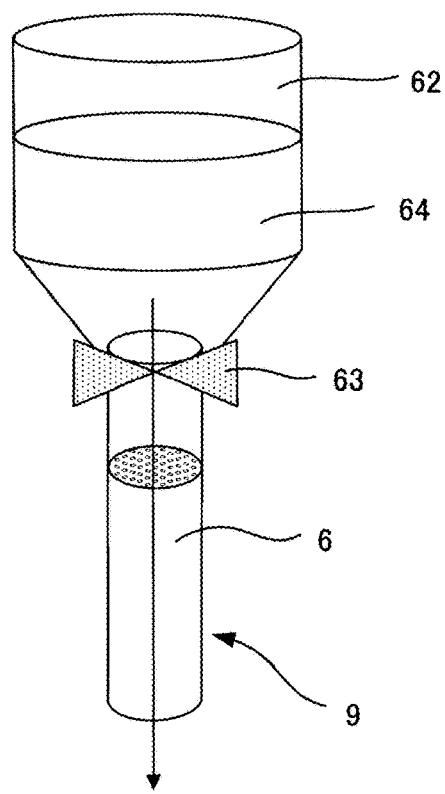
FIG. 3 is a schematic view showing a state where seeding slurry is poured in a particle adhesion step.

The seed crystal dispersion liquid prepared in (1) was diluted with ion-exchanged water or ethanol, adjusted to have a DDR concentration of 0.001 to 0.36 mass % (solid content in the slurry 64), and stirred with a stirrer at 300 rpm to obtain a seeding slurry liquid (slurry 64). The porous body 9 was fixedly attached to the lower end of a wide-mouth funnel 62, and 160 ml of the seeding slurry liquid was poured from above the porous body 9 and allowed to pass through the cells 4 (see FIG. 3). The porous body 9 where the slurry 64 flowed down was dried by sending wind in the cells for 10 to 30 minutes under the conditions of room temperature or 80° C. and a wind velocity of 3 to 6 m/s. Flowing down of the slurry 64 and drying by sending wind were repeated one to six times to obtain a sample. After drying, microstructure observation was performed with an electron microscope. Adhesion of DDR particles to the surface of the porous body 9 was confirmed.

(3) Membrane Formation (Membrane Forming Step)

After 7.35 g of ethylenediamine (produced by Wako Pure Chemical Industries, Ltd.) was put in a fluorine resin wide-mouthed bottle of 100 ml, 1.156 g of 1-adamantanamine (produced by Aldrich) was added and dissolved lest the precipitation of 1-adamantanamine should remain. After 98.0 g of 30 mass % colloidal silica (Snowtex S produced by Nissan Chemical Industries, Ltd.) and 116.55 g of ion-exchanged water were put in another vessel and lightly stirred, this was put in the wide-mouthed bottle containing the mixture of ethylenediamine and 1-adamantanamine, and they were shaken up strongly to prepare a raw material solution. The molar ratios of each component of the raw material solution were 1-adamantanamine/$SiO_2$=0.016 and water/$SiO_2$=21. Then, the wide-mouthed bottle containing the raw material solution was set in a homogenizer and stirred for one hour. The porous body 9 where DDR particles were allowed to adhere thereto in the above (2) was disposed in the stainless steel pressure resistant vessel 65 having a fluorine resin inner cylinder having an inner volume of 300 ml, and the prepared raw material solution (sol 67) was put in and subjected to a heating treatment (hydrothermal synthesis) at 140° C. for 50 hours (see FIG. 4). It is to be noted that it was alkaline at the time of hydrothermal synthesis due to colloidal silica and ethylenediamine of the raw material. A fracture surface of the porous body 9 where the membrane was formed was observed by a scanning electron microscope to find that the DDR membrane had a thickness of 10 μm or less.

(4) Removal of Structure-Directing Agent

The membrane formed was heated at 450 or 500° C. for 50 hours in an air atmosphere in an electric furnace to burn away 1-adamantanamine in the pores. The crystal phase was identified by X-ray diffraction and was confirmed to be DDR type zeolite. After forming the membrane, it was confirmed that the porous body 9 was coated with DDR type zeolite.

Examples 5 and 6

(Formation of Silica Membrane)

Next, as the separation membrane 33, a silica membrane was formed on the inner wall faces 4s. The precursor solution (silica sol solution) to form a silica membrane was prepared by subjecting tetraethoxysilane to hydrolysis in the presence of nitric acid to obtain a sol solution and diluting it with ethanol. The precursor solution (silica sol solution) to form the silica membrane was poured into the porous body 9 having the inner wall faces 4s formed therein from above and allowed to flow through the cells 4 to allow the precursor solution to adhere to the inner wall faces of the cells 4. Then, after temperature was raised at a rate of 100° C./hour and maintained at 500° C. for one hour, the temperature was lowered at a rate of 100° C./hour. Such operations of pouring, drying, raising temperature, and lowering temperature were repeated 3 to 5 times to form a silica membrane.

Example 7

(Formation of Carbon Membrane)

As the separation membrane 33, a carbon membrane was formed on the inner wall faces 4s of the cells 4. The precursor solution was obtained by mixing and dissolving a phenol resin in an organic solvent. By dip coating, the precursor solution to form a carbon membrane was brought into contact with the surface of the porous body 9 to form a membrane. Then, a thermal treatment at 300° C. for one hour was performed to dispose a polyimide resin as the precursor of the carbon membrane on the surface. The obtained polyimide resin layer-provided substrate was subjected to a thermal treatment at 600° C. for five hours in a non-oxidizing atmosphere to obtain the carbon membrane.

2. Defect Detection Method

Defects of the separation membrane structure 1 having a separation membrane 33 formed therein was detected by using a method of measuring the degree of vacuum or a method of measuring the gas permeation amount.

(Measurement of Degree of Vacuum)

As shown in FIG. 7, the degree of vacuum of each cell 4 was measured. Suction was performed on one side of the cells 4 by a vacuum pump (Model No. G-20DA produced by AS One Corporation, exhaust velocity of 24 L/min., ultimate pressure of $1.3 \times 10^{-1}$ Pa, two stage type), and a vacuum gauge (calibrator Model No. DP1800 produced by GE Sensing) is connected to the cells 4 on the other side so that the inside of the cells was vacuumed and the achieved degree of degree of vacuum inside the cell 4 was measured.

Figure 10A:
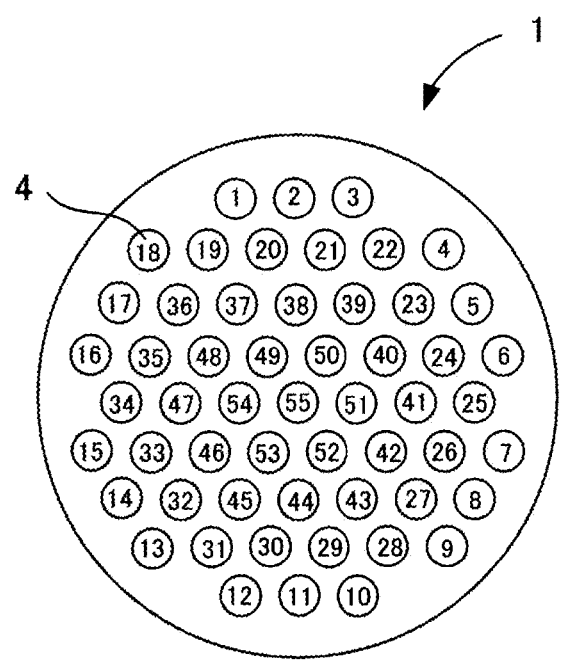
FIG. 10A is a view showing cell numbers of the cells of a monolithic separation membrane structure.

The average value of all the cells 4 and the standard deviation ($\sigma$) were calculated, and a cell with the degree of vacuum worse than "average value+$2\sigma$" (low-vacuum cell) was considered as a cell having a defect generated therein (more defects than the other cells 4). The results of Example 1 are shown in table 1. The cell numbers are as shown in FIG. 10A, and all the 55 cells 4 were checked for the degree of vacuum. Incidentally, the degrees of vacuum in the table are shown by gauge pressure (minus expression on the basis of air atmosphere).

TABLE 1

| Cell No. | Degree of vacuum (kPa) |
|---|---|
| 1 | −99.22 |
| 2 | −99.86 |
| 3 | −99.85 |
| 4 | −99.83 |
| 5 | −99.85 |
| 6 | −99.85 |
| 7 | −99.78 |
| 8 | −99.78 |
| 9 | −99.80 |
| 10 | −99.78 |
| 11 | −99.75 |
| 12 | −99.77 |
| 13 | −99.74 |
| 14 | −99.54 |
| 15 | −99.53 |
| 16 | −99.28 |
| 17 | −99.70 |
| 18 | −99.75 |
| 19 | −99.77 |
| 20 | −99.81 |
| 21 | −99.85 |
| 22 | −99.84 |
| 23 | −99.88 |
| 24 | −99.85 |
| 25 | −99.85 |
| 26 | −99.84 |
| 27 | −99.87 |
| 28 | −99.87 |
| 29 | −99.88 |
| 30 | −99.90 |
| 31 | −99.88 |
| 32 | −99.86 |
| 33 | −99.80 |
| 34 | −99.72 |
| 35 | −99.79 |
| 36 | −99.77 |
| 37 | −99.76 |
| 38 | −99.82 |
| 39 | −99.79 |
| 40 | −99.77 |
| 41 | −99.62 |
| 42 | −99.63 |
| 43 | −99.32 |
| 44 | −99.73 |
| 45 | −99.71 |
| 46 | −99.67 |
| 47 | −99.82 |
| 48 | −99.83 |
| 49 | −99.83 |

TABLE 1-continued

| Cell No. | Degree of vacuum (kPa) |
| --- | --- |
| 50 | −99.71 |
| 51 | −99.90 |
| 52 | −99.65 |
| 53 | −99.77 |
| 54 | −99.94 |
| 55 | −99.85 |
|  | kPa |
| Average value | −99.76 |
| σ | 0.15 |
| Average value + 2σ | −99.46 |

The average value of the degrees of vacuum of 55 cells 4 was −99.76 kPa, the standard deviation (σ) was 0.15 kPa, and the "average value+2σ" was −99.46 kPa. Therefore, the three cells 4 having cell numbers 1, 16, and 43 were considered to be defective.

(Measurement of Gas Permeation Amount)

As shown in FIG. 6, gas having a molecular size not smaller than the pore size of the membrane was introduced into the cells 4, and defects were checked from the gas permeation amount. In the case of a DDR membrane, tetrafluoromethane was used. First, one end of a cell 4 to be measured was plugged with a silicon plug, and, after the other end of the cell 4 was connected to a soap-film flowmeter, tetrafluoromethane was supplied at 0.2 MPa from the external surface of the monolithic substrate. The time that elapsed before 0.5 cc of the tetrafluoromethane leaked out of the cell was measured to calculate the permeation amount of the tetrafluoromethane. In the case of a silica membrane or a carbon membrane, sulfur hexafluoride was used.

Figure 10B:
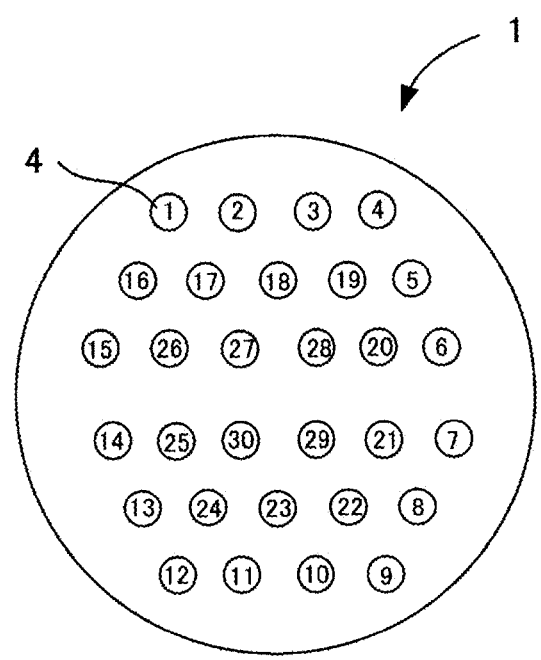
FIG. 10B is a view showing cell numbers of the cells of a monolithic separation membrane structure of another embodiment.

The average value of the permeation amount and the standard deviation (σ) of all the cells 4 were calculated, and the cell having a permeation amount greater than "average value+2σ" was considered as a cell having a defect generated therein (more defects than the other cells 4). The results of Example 3 are shown in Table 2. The cell numbers were as shown in FIG. 10B, and all the 30 cells 4 were checked for the permeation amount.

TABLE 2

| Cell No. | Tetrafluoromethane permeation amount ($L/m^2 \cdot s \cdot MPa$) |
| --- | --- |
| 1 | 0.0001 |
| 2 | 0.0009 |
| 3 | 0.0009 |
| 4 | 0.0010 |
| 5 | 0.0003 |
| 6 | 0.0001 |
| 7 | 0.0023 |
| 8 | 0.0001 |
| 9 | 0.0013 |
| 10 | 0.0023 |
| 11 | 0.0011 |
| 12 | 0.0011 |
| 13 | 0.0002 |
| 14 | 0.0015 |
| 15 | 0.0005 |
| 16 | 0.0012 |
| 17 | 0.0005 |
| 18 | 0.0008 |
| 19 | 0.0004 |
| 20 | 0.0011 |
| 21 | 0.0009 |
| 22 | 0.0008 |
| 23 | 0.0008 |
| 24 | 0.0005 |
| 25 | 0.0010 |
| 26 | 0.0009 |
| 27 | 0.0008 |
| 28 | 0.0009 |
| 29 | 0.0024 |
| 30 | 0.0020 |
|  | $L/m^2 \cdot s \cdot MPa$ |
| Average value | 0.0009 |
| σ | 0.0006 |
| Average value + 2σ | 0.0021 |

The average value of the permeation amounts of 30 cells 4 was 0.0009 $L/m^2 \cdot s \cdot MPa$, the standard deviation (σ) was 0.0006 $L/m^2 \cdot s \cdot MPa$, and the "average value+2σ" was 0.0021 $L/m^2 \cdot s \cdot MPa$. Therefore, the three cells 4 having cell numbers of 7, 10, and 29 were considered to be defective.

3. Repair Method, Effect

Regarding the examples (Examples 2 and 4 to 7) other than Example 1 (Table 1) and Example 3 (Table 2), defects were detected in the same manner, and the cells 4 considered to be defective were repaired.

(DDR Type Zeolite Membrane)

Example 1: Epoxy

An epoxy resin (E200 produced by Konishi Co., Ltd.) was poured into the three defective cells detected from the measurement of degree of vacuum of the separation membrane structure 1 up to 5 mm from one end face and dried at room temperature for 24 hours to seal the cells 4.

Example 2: Silicon Plug

Silicon plugs (Model 2 pink produced by AS ONE Corporation) formed into a conical shape in advance were inserted into the four defective cells detected from the measurement of degree of vacuum of the separation membrane structure 1 and fixed to seal the cells 4.

Example 3: Perfluor Plug

Perfluor plugs (produced by AIR WATER MACH INC.) formed into a conical shape in advance were inserted into the three defective cells detected from the measurement of gas permeation amount and fixed to seal the cells 4.

Example 4: Epoxy

Only Example 4 used a large-sized porous body 9 having an outer diameter of 180 mm, an entire length of 1000 mm, and 2050 cells having a cell diameter of 2.5 mm. An epoxy resin (E200 produced by Konishi Co., Ltd.) was poured into the 31 defective cells detected from the measurement of degree of vacuum of the separation membrane structure 1 up to 10 mm from an end face and dried at room temperature for 24 hours to seal the cells 4.

(Silica Membrane)

Example 5: Silicon Plug

Silicon plugs (Model 2 pink produced by AS ONE Corporation) formed into a conical shape in advance were inserted into the nine defective cells detected from the measurement of gas permeation amount of the separation membrane structure 1 and fixed to seal the cells 4.

Example 6: Perfluor Plug

Perfluor plugs (produced by AIR WATER MACH INC.) formed into a conical shape in advance were inserted into the seven defective cells detected from the measurement of degree of vacuum and fixed to seal the cells 4.
(Carbon Membrane)

Example 7: Silicon Plug

Silicon plugs (Model 2 pink produced by AS ONE Corporation) formed into a conical shape in advance were inserted into the three defective cells detected from the measurement of degree of vacuum of the separation membrane structure 1 and fixed to seal the cells 4.

(Separation Coefficient)

In the case where the separation membrane 33 was a DDR membrane, the separation coefficients before the repair and after the repair were obtained as follows. A mixed gas of carbon dioxide ($CO_2$) and methane ($CH_4$) (the volume ratio of carbon dioxide ($CO_2$) to methane ($CH_4$) was 50:50, and the partial pressure of each gas was 0.2 MPa) was introduced into the cells 4 of the separation membrane structure 1. The gas passed through the separation membrane structure 33 was collected to perform component analysis using a gas chromatography, and the separation coefficient was calculated from the formula of [separation coefficient $\alpha$=(permeated $CO_2$ concentration/permeated $CH_4$ concentration)/(supplied $CO_2$ concentration/supplied $CH_4$ concentration)].

In the case where the separation membrane 33 was a carbon membrane or a silica membrane, the separation coefficient was obtained as follows. A mixed liquid of water and ethanol was introduced into the cells 4 of the separation membrane structure 1, the liquid having passed through the separation membrane 33 was collected to perform component analysis using a gas chromatography. The separation coefficient was calculated from the formula of [separation coefficient $\alpha$=(permeated water concentration (mass %)/permeated ethanol concentration (mass %))/(supplied water concentration (mass %)/supplied ethanol concentration (mass %))].

(Separation Coefficient after Pressurization)

As shown in FIG. 2A, the repaired separation membrane 1 was housed in a cylindrical housing 51 having a fluid inlet 52 and a fluid outlet 53, and, after water was allowed to flow into the housing from the fluid inflow port 52 of the housing 51 to apply pressure of 5 MPa with water, drying was performed with a dryer. Then, the separation coefficient was calculated in the same manner as described above.

The separation coefficients before the repair, after the repair, and after the pressurization at 5 MPa with water are shown in Table 3.

TABLE 3

| Repairing material | Membrane type | Before repair Separation coefficient | After repair Separation coefficient | After pressurization at 5 MPa with water Separation coefficient |
|---|---|---|---|---|
| Example 1 Epoxy resin | DDR | 90 | 177 | 177 |
| Example 2 Silicon plug | DDR | 82 | 169 | 169 |

TABLE 3-continued

| Repairing material | Membrane type | Before repair Separation coefficient | After repair Separation coefficient | After pressurization at 5 MPa with water Separation coefficient |
|---|---|---|---|---|
| Example 3 Perfluor plug | DDR | 63 | 151 | 151 |
| Example 4 Epoxy resin | DDR | 112 | 186 | 186 |
| Example 5 Silicon plug | Silica | 95 | 159 | 159 |
| Example 6 Perfluor plug | Silica | 110 | 200 | 200 |
| Example 7 Silicon plug | Carbon | 236 | 314 | 314 |

As shown in Table 3, the separation coefficient has increased after the repair in comparison with that before the repair, and the effect of repair was confirmed. In addition, regarding the separation performance after pressurization at 5 MPa with water of the separation membrane structure 1 after repair, no decrease in the separation coefficient by the pressurization has been recognized. That is, it can be said that the withstand pressure for use (separation performance retention strength) was 5 MPa or more, and pressure resistance of the repaired portion was confirmed. In other words, the separation membrane structure 1 sealed with a polymer compound could withstand 5 MPa or more. Though not shown in the Tables, no problem due to pressurization at 5 MPa with water has caused regarding the gas permeation amount, too.

INDUSTRIAL APPLICABILITY

The defect detection method and the repair method of the present invention can be used for detection and repair of defects in a monolithic separation membrane structure having a separation membrane formed on the inner wall faces of the cells. The monolithic separation membrane structure of the present invention can be used for separation for a mixed gas or a mixed liquid.

DESCRIPTION OF REFERENCE NUMERALS

1: separation membrane structure, 1s: sealing portion, 2, 2a, 2b: end face, 3: partition wall, 4: cell, 4a: separation cell, 4b: water collection cell, 4s: inner wall face, 6: outer peripheral face, 7: discharge passage, 8: plugging portion, 9: porous body, 21: plug, 21a: (hole-formed) plug, 22: flowmeter, 23: gas cylinder, 25: vacuum pump, 26: vacuum gauge, 27: polymer compound, 30: substrate, 33: separation membrane, 51: housing, 52: fluid inflow port, 53, 58: fluid outflow port, 54: sealing member, 62: wide-mouth funnel, 63: cock, 64: slurry, 65: pressure resistant vessel, 67: sol, 68: dryer.

The invention claimed is:

1. A monolithic separation membrane structure comprising:
   a monolithic substrate having a plurality of cells defined and formed by porous partition walls from one end face to an other end face in a longitudinal direction, and a separation membrane formed on inner wall faces of the cells;
   wherein both end portions of cells that have defects in the separation membrane are sealed with sealing members through which fluid does not pass, and the sealing members extend into each of the cells that have defects at least 1 mm from each respective end face, and
   wherein the sealing members are of polymer compound.

2. The monolithic separation membrane structure according claim 1, wherein the polymer compound is a synthetic resin.

3. The monolithic separation membrane structure according to claim 2, wherein the synthetic resin is one of epoxy, silicon-based, and fluorine-based resins.

4. The monolithic separation membrane structure according to claim 1, wherein the separation membrane is formed of an inorganic material.

5. The monolithic separation membrane structure according to claim 4, wherein the inorganic material is one of zeolite, carbon, and silica.

6. The monolithic separation membrane structure according to claim 4, wherein the monolithic substrate is of a porous ceramic.

7. The monolithic separation membrane structure according to claim 4, having a withstand pressure for use of 1 MPa or more.

8. The monolithic separation membrane structure according to claim 1, wherein the monolithic substrate is of a porous ceramic.

9. The monolithic separation membrane structure according to claim 8, having a withstand pressure for use of 1 MPa or more.

10. The monolithic separation membrane structure according to claim 1, having a withstand pressure for use of 1 MPa or more.

11. The monolithic separation membrane structure according to claim 1, wherein the sealing members completely fill the cells that have defects.

12. The monolithic separation membrane structure according to claim 1,
wherein the plurality of cells includes separation cells and water collection cells, and both end portions of the separation cells that have defects in the separation membrane are sealed with the sealing members.

* * * * *